(12) United States Patent
Lee et al.

(10) Patent No.: US 7,914,506 B2
(45) Date of Patent: Mar. 29, 2011

(54) SPRAYING TYPE NOSE RINSING APPARATUS

(75) Inventors: Jui-Jen Lee, Danshuei Township, Taipei County (TW); To-Chan Chen, Taipei (TW)

(73) Assignee: DTC-Healthkare Inc., Taipei (TW)

( * ) Notice: Subject to any disclaimer, the term of this patent is extended or adjusted under 35 U.S.C. 154(b) by 602 days.

(21) Appl. No.: 11/946,900

(22) Filed: Nov. 29, 2007

(65) Prior Publication Data
US 2009/0108097 A1    Apr. 30, 2009

(30) Foreign Application Priority Data
Oct. 29, 2007    (TW) ................................ 96218151 U

(51) Int. Cl.
*A61M 11/00*    (2006.01)

(52) U.S. Cl. ...................... 604/290; 604/94.01; 604/257; 604/258; 604/275; 604/276; 239/153

(58) Field of Classification Search ............... 604/94.01, 604/217, 275–276, 257–258, 77–79; 239/120–121, 239/153
See application file for complete search history.

(56) References Cited

U.S. PATENT DOCUMENTS

| | | | | |
|---|---|---|---|---|
| 321,850 | A * | 7/1885 | Philbrick | 604/276 |
| 935,227 | A * | 9/1909 | Pfeifer | 604/257 |
| 989,839 | A * | 4/1911 | Fowler | 604/276 |
| 1,185,649 | A * | 6/1916 | Fowler | 604/257 |
| 1,232,151 | A * | 7/1917 | Wood | 4/626 |
| 1,487,252 | A * | 3/1924 | Lore | 604/35 |
| 1,502,163 | A * | 7/1924 | Sprague | 604/36 |
| 1,599,787 | A * | 9/1926 | Meyer | 604/217 |
| 1,603,758 | A * | 10/1926 | Fisher | 604/36 |
| 2,078,180 | A * | 4/1937 | Kronenberg | 604/28 |
| 2,560,746 | A * | 7/1951 | Scarkino | 604/212 |
| 3,847,145 | A * | 11/1974 | Grossan | 601/160 |
| 4,029,095 | A * | 6/1977 | Pena | 604/30 |
| 4,684,362 | A * | 8/1987 | Holt | 604/540 |
| 4,844,345 | A * | 7/1989 | Waldrum | 239/121 |
| 5,112,322 | A * | 5/1992 | Hathaway | 604/317 |
| 5,417,652 | A * | 5/1995 | Scott, Sr. | 604/19 |
| 5,697,921 | A * | 12/1997 | Blair | 604/317 |
| 5,899,878 | A * | 5/1999 | Glassman | 604/48 |
| 5,928,190 | A * | 7/1999 | Davis | 604/94.01 |
| 6,328,718 | B1 * | 12/2001 | Chiang et al. | 604/319 |
| 6,361,521 | B1 * | 3/2002 | Erickson | 604/37 |
| 6,776,778 | B2 * | 8/2004 | Prince | 604/514 |
| 2002/0077621 | A1 * | 6/2002 | Prince | 604/514 |
| 2002/0198488 | A1 * | 12/2002 | Yao | 604/35 |
| 2003/0225427 | A1 * | 12/2003 | Chen | 606/162 |
| 2005/0124974 | A1 * | 6/2005 | Holman | 604/514 |
| 2007/0131230 | A1 * | 6/2007 | Giroux | 128/207.13 |
| 2007/0299396 | A1 * | 12/2007 | Rocklin | 604/131 |
| 2008/0029086 | A1 * | 2/2008 | Harlan et al. | 128/200.22 |
| 2008/0154183 | A1 * | 6/2008 | Baker et al. | 604/28 |
| 2008/0221507 | A1 * | 9/2008 | Hoke et al. | 604/28 |

* cited by examiner

*Primary Examiner* — Tatyana Zalukaeva
*Assistant Examiner* — Paula L Craig
(74) *Attorney, Agent, or Firm* — Alan Kamrath; Kamrath & Associates PA

(57) ABSTRACT

A nose rinsing apparatus includes a main container provided with a receiving space to receive a nose rinsing liquid, a spraying device mounted on the main container to spray the atomized nose rinsing liquid, and a recycle container mounted on the main container and having an inside provided with an opening and a periphery provided with at least one three-dimensional concave portion. Thus, the three-dimensional concave portion of the recycle container has an ergonomically designed shape to fit that of the user's upper jaw so that the three-dimensional concave portion of the recycle container abuts the user's upper jaw closely and entirely to prevent the wasted rinsing liquid and the dirt in the user's nose from leaking outwardly from the opening of the recycle container.

9 Claims, 5 Drawing Sheets

SPRAYING TYPE NOSE RINSING APPARATUS

This application claims priority to Taiwan application No. 096218151 filed Oct. 29, 2007.

BACKGROUND OF THE INVENTION

1. Field of the Invention

The present invention relates to a nose rinsing apparatus and, more particularly, to a spraying type nose rinsing apparatus.

2. Description of the Related Art

A conventional spraying type nose rinsing apparatus in accordance with the prior art shown in FIG. 6 comprises a main container 10 having an inside provided with a receiving space to receive a nose rinsing liquid, a spraying device 20 mounted on an upper end of the main container 10 to suck and atomize the nose rinsing liquid in the receiving space of the main container 10 and to spray outwardly the nose rinsing liquid that is atomized, and a recycle container 4 mounted on the upper end of the main container 10 and located under the spraying device 20. The spraying device 20 includes an upper seat 201 mounted on the upper end of the main container 10, an air pipe 202 mounted on the upper seat 201, a spraying head 204 mounted on the upper seat 201 and connected to the air pipe 202, and a mounting sleeve 205 mounted on the upper seat 201 and enclosed around the spraying head 204 to support the spraying head 204. The recycle container 4 has a circular top provided with a separation plate 41 having a plurality of permeation holes 42 connected to a hollow inside of the recycle container 4.

In operation, the spraying device 20 sucks and atomizes the nose rinsing liquid in the receiving space of the main container 10 by a motorized mechanism or by a manual action. Thus, when a user's nose abuts the spraying head 204 of the spraying device 20, the atomized rinsing liquid from the spraying head 204 of the spraying device 20 is injected into the user's nose to flush and rinse the user's nose, and the wasted rinsing liquid and the dirt in the user's nose are introduced through the permeation holes 42 into the recycle container 4.

However, the outer face of the recycle container 4 has a substantially three-dimensional convex shape, and the user's face also has a substantially three-dimensional convex shape. Thus, the user's upper jaw (between the nose and the mouth) cannot abut the outer face of the recycle container 4 closely and completely, so that the wasted rinsing liquid and the dirt in the user's nose easily leak outwardly from the recycle container 4 and cannot be gathered by the recycle container 4 efficiently, thereby causing a sanitary problem.

BRIEF SUMMARY OF THE INVENTION

In accordance with the present invention, there is provided a nose rinsing apparatus, comprising a main container having an inside provided with a receiving space to receive a nose rinsing liquid, a spraying device mounted on an open upper end of the receiving space of the main container to suck and atomize the nose rinsing liquid in the receiving space of the main container and to spray outwardly the nose rinsing liquid that is atomized, and a recycle container mounted on a side of the main container and having an inside provided with an opening and a periphery provided with at least one three-dimensional concave portion.

The primary objective of the present invention is to provide a nose rinsing apparatus, wherein the three-dimensional concave portion of the recycle container has an ergonomically designed shape to fit that of the user's upper jaw so that the three-dimensional concave portion of the recycle container abuts the user's upper jaw closely and entirely to prevent the wasted rinsing liquid and the dirt in the user's nose from leaking outwardly from the opening of the recycle container.

Another objective of the present invention is to provide a nose rinsing apparatus, wherein the spraying head of the spraying device has an upward inclined angle of about twenty to thirty degrees (20° to 30°) relative to a horizontal face of the upper seat so that the atomized rinsing liquid from the spraying head of the spraying device is directly toward the user's nose to flush and rinse the user's nose smoothly, thereby providing a comfortable sensation to the user.

A further objective of the present invention is to provide a nose rinsing apparatus, wherein the wasted rinsing liquid and the dirt in the user's nose the opening of the recycle container are introduced into the opening of the recycle container completely and entirely so as to satisfy the sanitary requirement.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
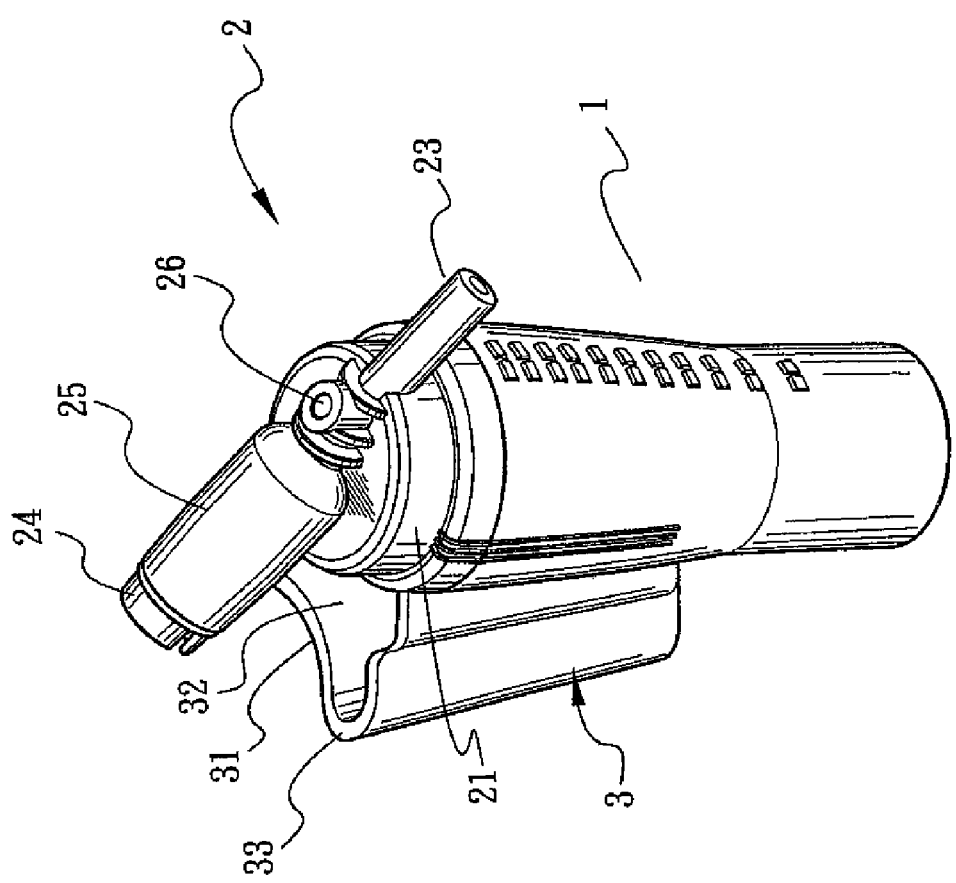
FIG. 1 is a perspective view of a nose rinsing apparatus in accordance with the preferred embodiment of the present invention.
Figure 2:
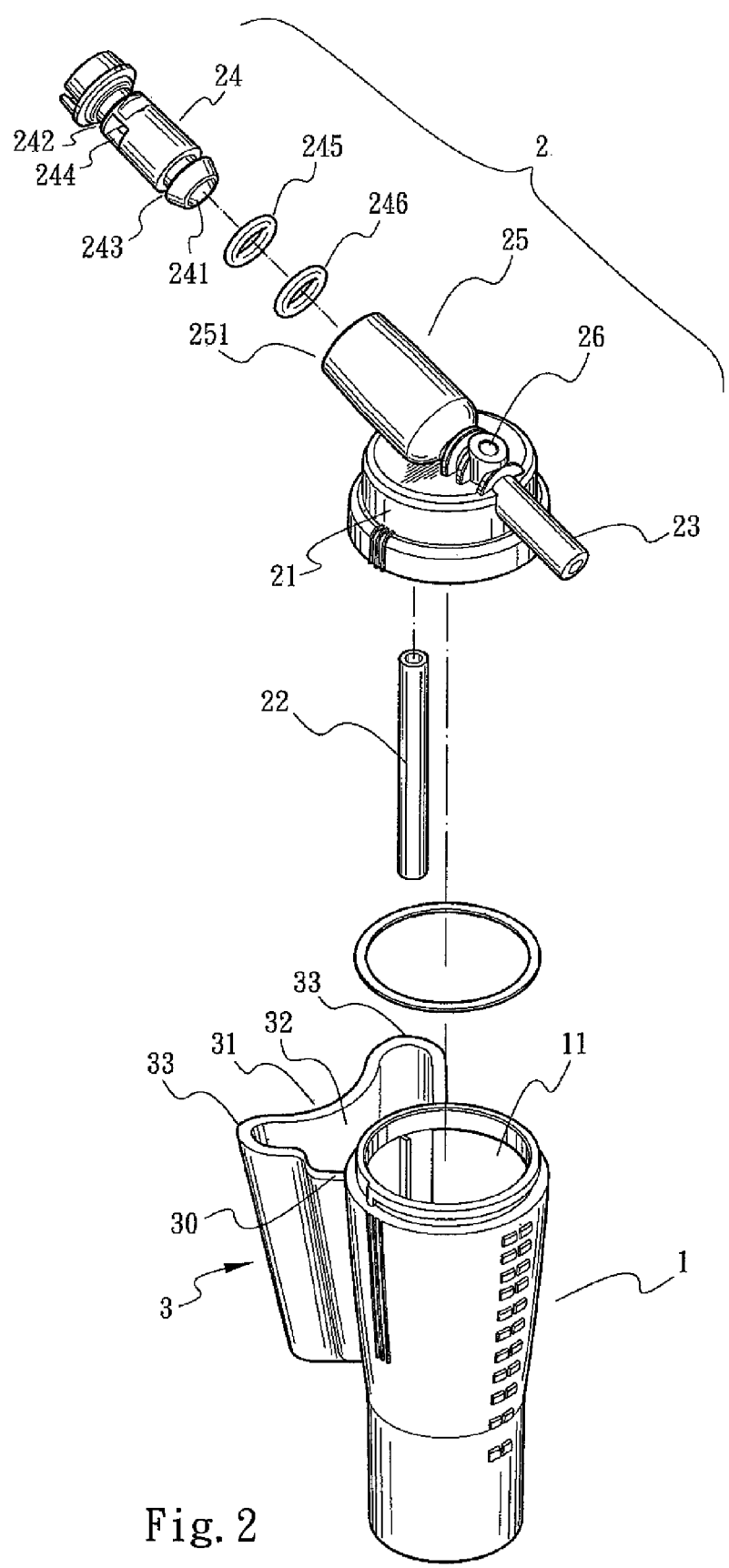
FIG. 2 is an exploded perspective view of the nose rinsing apparatus as shown in FIG. 1.
Figure 3:
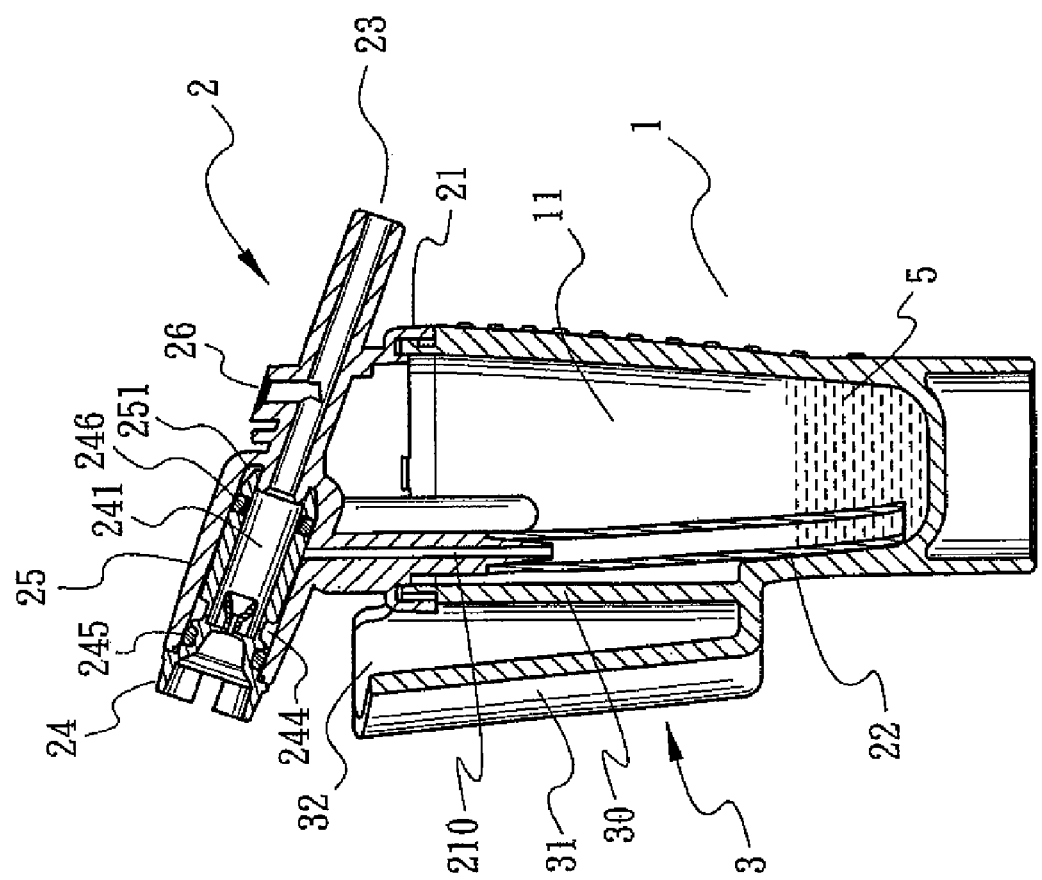
FIG. 3 is a front cross-sectional view of the nose rinsing apparatus as shown in FIG. 1.

Referring to the drawings and initially to FIGS. 1-3, a spraying (or atomizing) type nose rinsing apparatus in accordance with the preferred embodiment of the present invention comprises a main container 1 having an inside provided with a receiving space 11 to receive a nose rinsing liquid 5, a spraying device 2 mounted on an open upper end of the receiving space 11 of the main container 1 to suck and atomize the nose rinsing liquid 5 in the receiving space 11 of the main container 1 and to spray outwardly the nose rinsing liquid 5 that is atomized, and a recycle container 3 mounted on a side of the main container 1 and having an inside provided with an opening 32 and a periphery provided with at least one three-dimensional concave portion 31.

The spraying device 2 includes an upper seat 21 mounted on the open upper end of the receiving space 11 of the main container 1, an air pipe 23 mounted on the upper seat 21, a relief valve 26 mounted on and connected to the air pipe 23 to regulate an air drain rate the air pipe 23, a spraying head 24 mounted on the upper seat 21 and having an inside provided with an atomizing air channel 241 connected to the air pipe 23 and a peripheral wall provided with at least one connecting hole 244 connected to the atomizing air channel 241, a mounting sleeve 25 mounted on the upper seat 21 and enclosed around the spraying head 24 to support the spraying head 24, a conducting pipe 22 mounted in the receiving space 11 of the main container 1 and having a first end connected to the nose rinsing liquid 5 and a second end connected to the mounting sleeve 25 and the connecting hole 244 of the spraying head 24, and two O-rings 245 and 246 mounted between the spraying head 24 and the mounting sleeve 25 to provide a sealing effect.

The upper seat 21 of the spraying device 2 has a side provided with a conduit 210 connected between the conducting pipe 22 and the connecting hole 244 of the spraying head 24 to connect the conducting pipe 22 to the connecting hole 244 of the spraying head 24. The mounting sleeve 25 of the spraying device 2 has a inside provided with a mounting chamber 251 for mounting the spraying head 24. The spraying head 24 of the spraying device 2 has an outer wall provided with two spaced annular grooves 242 and 243 for mounting the two O-rings 245 and 246. The connecting hole 244 of the spraying head 24 and the conduit 210 of the upper seat 21 are located between the two O-rings 245 and 246. The spraying head 24 of the spraying device 2 is located above the upper seat 21 and has an upward inclined angle of about twenty to thirty degrees (20° to 30°) relative to a horizontal face of the upper seat 21.

The recycle container 3 suspends and protrudes outwardly from a periphery of the main container 1. The recycle container 3 and the main container 1 are formed integrally or separated from each other. Alternatively, the recycle container 3 is attached to and combined with the periphery of the main container 1. The opening 32 of the recycle container 3 is located under the spraying head 24 of the spraying device 2 and has an open upper end. The three-dimensional concave portion 31 of the recycle container 3 extends longitudinally through a whole length of the recycle container 3 and has an ergonomically designed shape to fit that of an upper jaw (between the nose and the mouth) of a user's face. The recycle container 3 has a first side 30 attached to the periphery of the main container 1 and a second side located opposite to the first side 30 and provided with the three-dimensional concave portion 31. The opening 32 of the recycle container 3 is located between the first side 30 and the three-dimensional concave portion 31 of the recycle container 3. The three-dimensional concave portion 31 of the recycle container 3 has two opposite ends each provided with an arcuate protruding portion 33 abutting the upper jaw of the user's face smoothly.

Figures 4, 5:
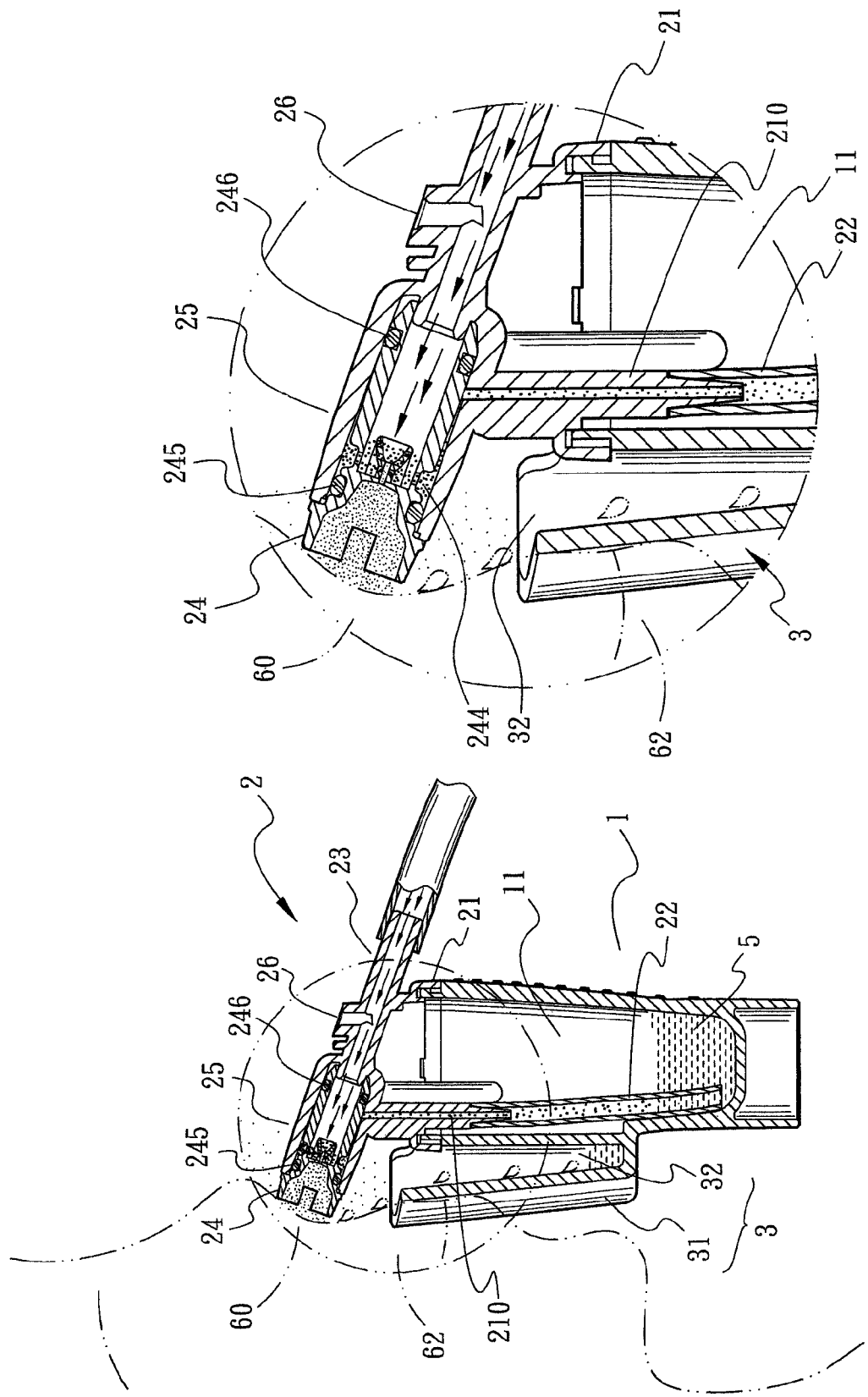
FIG. 4 is a schematic operational view of the nose rinsing apparatus as shown in FIG. 3.
FIG. 5 is a locally enlarged view of the nose rinsing apparatus as shown in FIG. 4.
Figure 6:
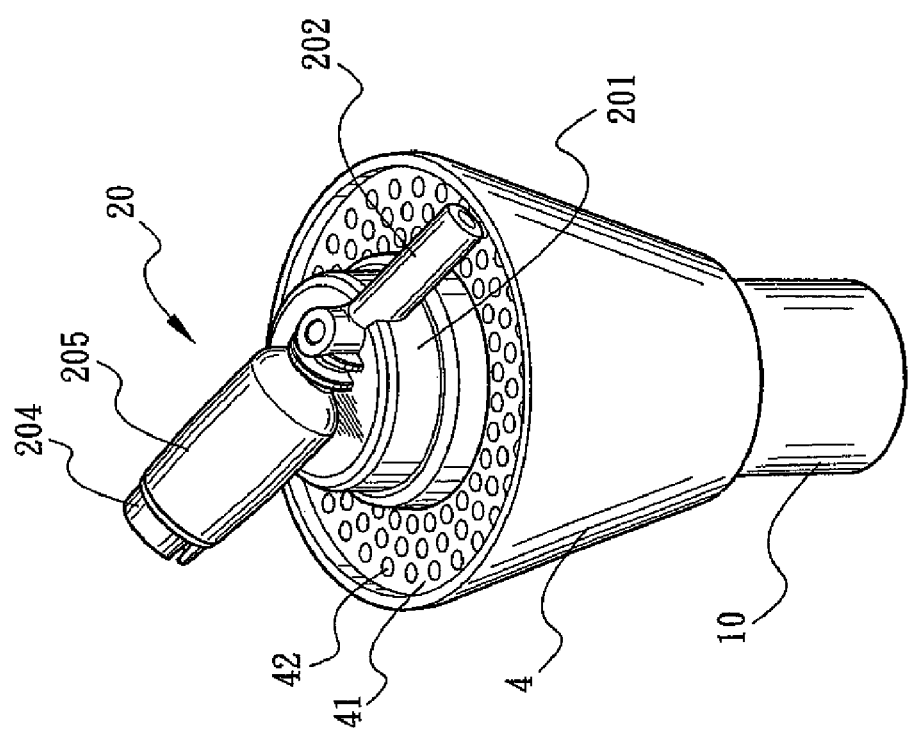
FIG. 6 is a perspective view of a conventional nose rinsing apparatus in accordance with the prior art.

In operation, referring to FIGS. 4 and 5 with reference to FIGS. 1-3, the spraying device 2 sucks and atomizes the nose rinsing liquid 5 in the receiving space 11 of the main container 1 by a motorized mechanism or by a manual action. Thus, when a user's nose 60 abuts the spraying head 24 of the spraying device 2, the opening 32 of the recycle container 3 faces the user's nose 60 directly, the atomized rinsing liquid 5 from the spraying head 24 of the spraying device 2 is injected into the user's nose 60 to flush and rinse the user's nose 60, and the wasted rinsing liquid 5 and the dirt in the user's nose 60 are introduced into the opening 32 of the recycle container 3.

Accordingly, the three-dimensional concave portion 31 of the recycle container 3 has an ergonomically designed shape to fit that of the user's upper jaw 62 so that the three-dimensional concave portion 31 of the recycle container 3 abuts the user's upper jaw 62 closely and entirely to prevent the wasted rinsing liquid 5 and the dirt in the user's nose 60 from leaking outwardly from the opening 32 of the recycle container 3. In addition, the spraying head 24 of the spraying device 2 has an upward inclined angle of about twenty to thirty degrees (20° to 30°) relative to a horizontal face of the upper seat 21 so that the atomized rinsing liquid 5 from the spraying head 24 of the spraying device 2 is directly toward the user's nose 60 to flush and rinse the user's nose 60 smoothly, thereby providing a comfortable sensation to the user. Further, the wasted rinsing liquid 5 and the dirt in the user's nose 60 the opening 32 of the recycle container 3 are introduced into the opening 32 of the recycle container 3 completely and entirely so as to satisfy the sanitary requirement.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. A nose rinsing apparatus, comprising:
  a main container having an inside provided with a receiving space to receive a nose rinsing liquid;
  a spraying device mounted on an open upper end of the receiving space of the main container to suck and atomize the nose rinsing liquid in the receiving space of the main container and to spray outwardly the nose rinsing liquid that is atomized;
  a recycle container mounted on a side of the main container and having an inside provided with an opening and a periphery provided with at least one three-dimensional concave portion; wherein
  the recycle container has a first side attached to the periphery of the main container and a second side located opposite to the first side and provided with the three-dimensional concave portion;
  the opening of the recycle container is located between the first side of the recycle container and the three-dimensional concave portion of the recycle container;
  the opening of the recycle container has an open upper end, the open upper end of the recycle container being dimensioned and configured to collect the nose rinsing liquid after the nose rinsing liquid has been sprayed into a nose of a user;
  the three-dimensional concave portion of the recycle container has an ergonomically designed shape to fit that of an upper jaw of a user's face.

2. The nose rinsing apparatus in accordance with claim 1, wherein the recycle container suspends and protrudes outwardly from a periphery of the main container.

3. The nose rinsing apparatus in accordance with claim 1, wherein the recycle container and the main container are formed integrally.

4. The nose rinsing apparatus in accordance with claim 1, wherein the recycle container and the main container are separated from each other.

5. The nose rinsing apparatus in accordance with claim 1, wherein the recycle container is attached to and combined with a periphery of the main container.

6. The nose rinsing apparatus in accordance with claim 1, wherein the three-dimensional concave portion of the recycle container extends longitudinally through a whole length of the recycle container.

7. The nose rinsing apparatus in accordance with claim 1, wherein the three-dimensional concave portion of the recycle container has two opposite ends each provided with an arcuate protruding portion abutting the upper jaw of the user's face smoothly.

8. The nose rinsing apparatus in accordance with claim 1, wherein
  the spraying device includes an upper seat mounted on the open upper end of the receiving space of the main container, an air pipe mounted on the upper seat, a spraying head mounted on the upper seat and connected to the air pipe;

the opening of the recycle container is located under the spraying head of the spraying device.

9. The nose rinsing apparatus in accordance with claim 8, wherein the spraying head of the spraying device is located above the upper seat and has an upward inclined angle of about twenty to thirty degrees (20° to 30°) relative to a horizontal face of the upper seat.

* * * * *